United States Patent [19]

Stephen

[11] 3,956,361

[45] May 11, 1976

[54] HINDERED PHENOLIC DERIVATIVES OF NORBORNANE THIOALCOHOLS

[75] Inventor: John F. Stephen, New City, N.Y.

[73] Assignee: Ciba-Geigy Corporation, Ardsley, N.Y.

[22] Filed: May 23, 1974

[21] Appl. No.: 472,558

[52] U.S. Cl. .................. 260/473 S; 260/45.85 B; 44/70; 252/407
[51] Int. Cl.² ......................................... C07C 69/76
[58] Field of Search .......................... 260/473 S

[56] References Cited
UNITED STATES PATENTS 3,285,855  11/1966  Dexter et al. .................. 260/473 S

FOREIGN PATENTS OR APPLICATIONS 288,839   4/1967  Australia ........................ 260/473 S
1,337,163  7/1963  France
1,436,393  3/1966  France ........................... 260/473 S

OTHER PUBLICATIONS

Fieser, "Organic Chemistry", 3rd Ed., (1958), pp. 46–47.

Primary Examiner—John F. Terapane
Attorney, Agent, or Firm—Luther A. R. Hall

[57] ABSTRACT

Compounds having the formula

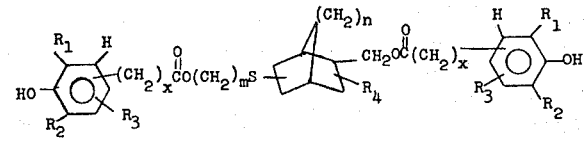

wherein $R_1$ and $R_2$ are independently the same or different alkyl groups of 1 to 8 carbon atoms, cycloalkyl of 5 to 6 carbon atoms or one of $R_1$ and $R_2$ is hydrogen, $R_3$ is hydrogen or lower alkyl of 1 to 6 carbon atoms, $R_4$ is hydrogen or a group

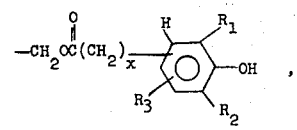

$m$ is 1 to 6, $n$ is 0 to 2 and $x$ is 1 to 2 are good thermal and oxidative stabilizers for synthetic polymers.

11 Claims, No Drawings

HINDERED PHENOLIC DERIVATIVES OF NORBORNANE THIOALCOHOLS

This invention related to hindered phenol norbornane derivatives and organic materials normally subject to oxidative and thermal degradation stabilized with said derivatives. The compounds of this invention can be represented by the formula I

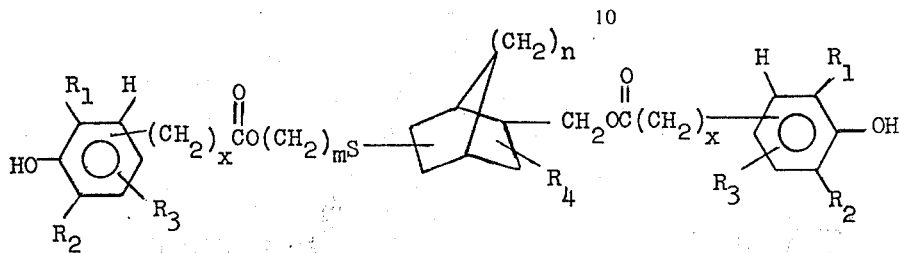
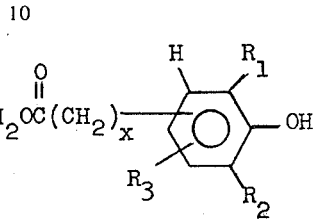

(I)

wherein $R_1$ and $R_2$ are independently the same or different alkyl groups of from 1 to 8 carbon atoms, cycloalkyl of from 5 to 6 carbon atoms or one of $R_1$ and $R_2$ is hydrogen, $R_3$ is hydrogen or lower alkyl of from 1 to 6 carbon atoms, providing that $R_3$ may be in either the meta or para position of the aromatic ring relevant to the hydroxyl group and that the side chain groups

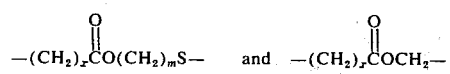

are located on the carbon adjacent to that of the $R_3$ group, $R_4$ is hydrogen or a group

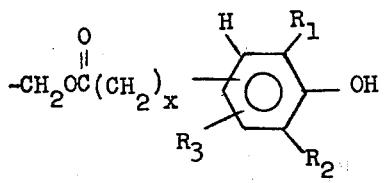

$m$ has a value of 1 to 6,
$n$ has a value of 0 to 2, and
$x$ has a value of 1 to 2.

The $R_1$ and $R_2$ groups can be straight or branched chain alkyl groups having 1 to 8 carbon atoms as for example methyl, ethyl, n-propyl, isopropyl, n-butyl, tert-butyl, n-hexyl and tert-octyl, or cycloalkyl of 5 to 6 carbon atoms such as cyclopentyl and cyclohexyl. Preferably $R_1$ and $R_3$ are lower alkyl groups of from 1 to 4 carbon atoms as for example, methyl, isopropyl and tert-butyl. Most preferably $R_1$ is tert-butyl and $R_2$ is tert-butyl or methyl.

$R_3$ can be lower alkyl of from 1 to 6 carbon atoms, such as methyl, ethyl, n-propyl, n-butyl and n-hexyl. The position of the $R_3$ group may be in either the meta or para position of the aromatic ring relevant to the hydroxyl group and the side chains

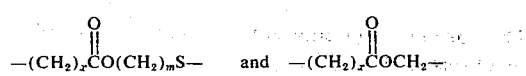

are located on the carbon adjacent to that of the $R_3$ group. The exact locations of $R_3$ and these side chain groups have no adverse affect on the stabilizer activity of the compounds of this invention. Preferably $R_3$ is hydrogen or methyl.

Perferably $m$ has a value of 2 to 6 and most preferably 2. Preferably $n$ has a value of 1. Preferably $x$ has a value of 2.

Compounds of this invention are made by reacting an unsaturated alcohol of formula II

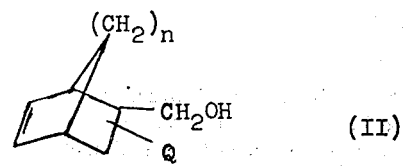

wherein $n$ has a value of 0 to 2 and where Q is hydrogen or a hydroxymethyl group with a mercaptoalcohol of formula III

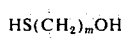         (III)

wherein $m$ has a value of 1 to 6 using a free radical catalyst, such as $\alpha,\alpha'$-azobisisobutyronitrile or a peroxide initiator, such as benzoyl peroxide, in a suitable solvent, such as dioxane or a suitable hydrocarbon, to form an intermediate of formula IV

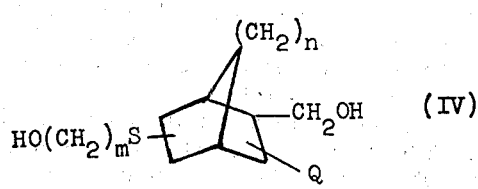

The position of the group Q may be on the same carbon as the denoted hydroxymethyl group or on the adjacent non-bridgehead carbon. Likewise the location of the $HO(CH_2)_mS$— group may be on either of the two carbon atoms between which the group is denoted in formula IV and may exist as a mixture of the two formula isomers. The exact location of the $HO(CH_2)_mS$— group has no adverse affect on the stabilizer activity of the compounds of this invention.

The compounds of formula I are conveniently prepared by the transesterification of an intermediate of formula IV with an ester formula V.

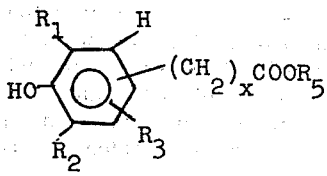

(V)

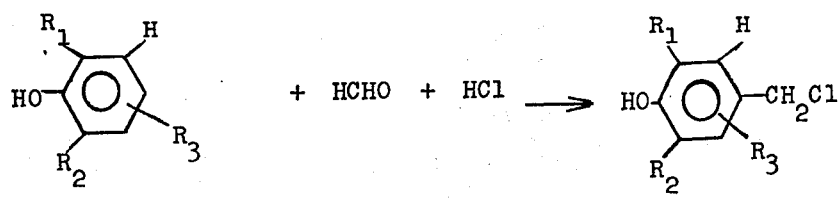

(A)

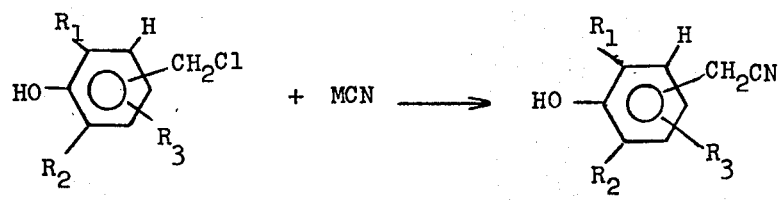

(B)

wherein $R_1$, $R_2$ and $R_3$ are as previously described, $R_5$ is alkyl with 1 to 8 carbon atoms and $x$ has a value of 1 to 2, in the presence of an alkali metal alkoxide, amide or hydride, preferably lithium hydride. $R_5$ is preferably methyl.

2-Hydroxymethyl-5-norbornene and 5-norobrnene2,2-dimethanol are commercially available.

5-Norbornene-endo-2,3-dicarboxylic acid anhydride, cis-$\Delta^4$-tetrahydrophthalic anhydride and bicyclo[2.2.2]-oct-5-ene-endo-2,3-dicarboxylic acid anhydride are commercially available. Each of the above materials is reduced using lithium aluminum hydride to prepare respectively 5-norbornene-2,3-dimethanol, cyclohex-4-ene-1,2-dimethanol and bicyclo [2.2.2]oct-5-ene-2,3-dimethanol as described by J. A. Stewart and P. Wilder, Jr., *J. Amer. Chem. Soc.*, 82, 2541(1960).

The preferred mercaptoalcohol, 2-mercaptoethanol, is commercially available.

Compounds of formula I which are of particular interest from a practical point of view because of ready availability of starting materials and ease of manufacture are those where $R_1$ and $R_2$ are lower alkyl of from 1 to 4 carbon atoms, $R_3$ is hydrogen and the side chain groups

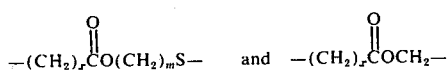

are in the para position of the aromatic ring relevent to the hydroxyl group.

The esters of formula V are made by the teachings of U.S. Pat. Nos. 3,247,240, 3,330,859 and 3,364,250. Especially useful as an intermediate in the preparation of the compounds of this invention are methyl 3,5-di-tert-butyl-4-hydroxyhydrocinnamate, methyl 3-methyl-5-tert-butyl-4-hydroxyhydrocinnamate and methyl 3,5-di-tert-butyl-4-hydroxyphenylacetate.

Where $x$ is 1, the esters are conveniently prepared by the reaction sequence represented by reactions A, B and C.

where M is an alkali metal such as sodium or potassium,

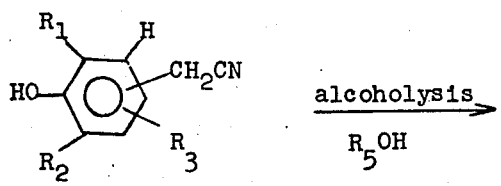

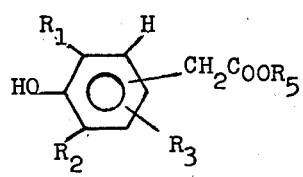

(C)

When the esters of formula V have the structure VI

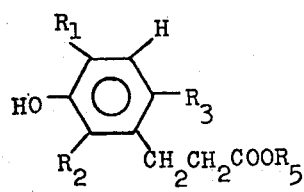

(VI)

They are conveniently prepared using the sequence of reactions D, E and F.

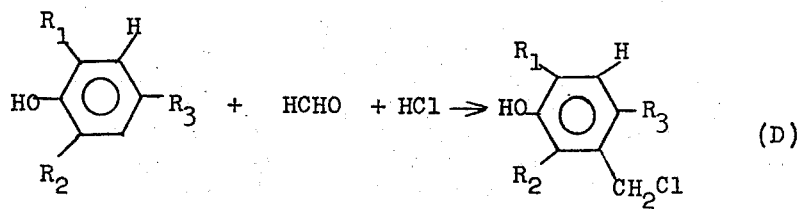

(D)

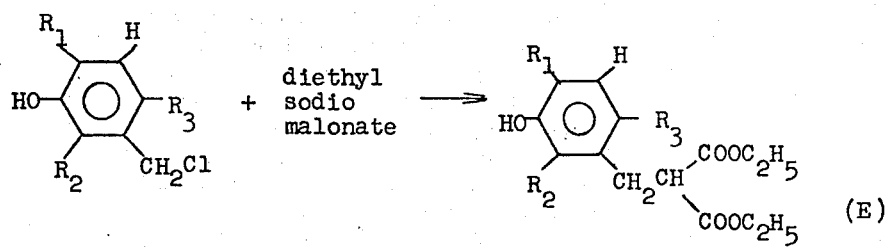

(E)

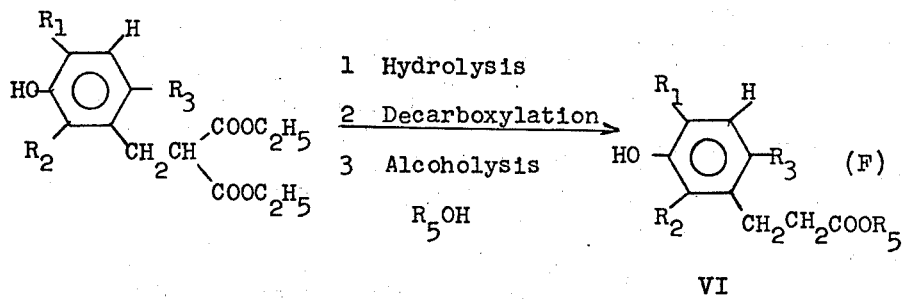

(F)

Listed below are illustrative examples of the compounds of this invention.

2-(3',5'-di-tert-butyl-4'-hydroxyhydrocinnamoyloxymethyl)-5 or 6-[6''-(3',5'-di-tert-butyl-4'-hydroxyhydrocinnamoyloxy)hexylthio]norbornane.

2-(3'-methyl-5'-tert-butyl-4'-hydroxyhydrocinnamoyloxymethyl)-5 or 6-[4''-(3'-methyl-5'-tert-butyl-4'-hydroxyhydrocinnamoyloxy)butylthio]norbornane.

2-(3',5'-di-tert-butyl-4'-hydroxyphenylacetoxymethyl)-5 or 6-[2''-(3',5'-di-tert-butyl-4'-hydroxyphenylacetoxy)ethylthio]norbornane.

2,3-di(3'-methyl-5'-tert-butyl-4'-hydroxyphenylacetoxymethyl)-5-[2''-(3'-methyl-5'-tert-butyl-4'-hydroxyphenylacetoxy)ethylthio]norbornane.

2,2-di(3',5'-di-tert-butyl-4'-hydroxyphenylacetoxymethyl)-5 or 6-[6''-(3',5'-di-tert-butyl-4'-hydroxyphenylacetoxy)hexylthio]norbornane.

2,(2'-methyl-5'-tert-octyl-4'-hydroxyhydrocinnamoyloxymethyl)-5 or 6-[2''-(2'-methyl-5'-tert-octyl- 4'-hydroxyhydrocinnamoyloxy)ethylthio]norbornane.

2,3-di(2'-methyl-5'-tert-butyl-4'-hydroxyhydrocinnamoyloxymethyl)-5-[2''-(2'-methyl-5''-tert-butyl-4'-hydroxyhydrocinnamoyloxy)ethylthio]norbornane.

2,2-di(2',3'-dimethyl-5'-tert-butyl-4'-hydroxyhydrocinnamoyloxymethyl)-5 or 6-[2''-(2',3'-dimethyl-5'-tert-butyl-4'-hydroxyhydrocinnamoyloxy)ethylthio]norbornane.

2-(2',6'-dimethyl-4'-tert-butyl-3'-hydroxyphenylacetoxymethyl)-5 or 6-[2''-(2',6'-dimethyl-4-tert-butyl-3'-hydroxyphenylacetoxy)ethylthio]norbornane.

2,3-di(6'-n-hexyl-4'-tert-butyl-3'-hydroxyphenylacetoxymethyl)-5-[2''-(6'-n-hexyl-4'-tert-butyl-3'-hydroxyphenylacetoxy)ethylthio]norbornane.

2-(3'-cyclohexyl-5'-tert-butyl-4'-hydroxyhydrocinnamoyloxymethyl)-5 or 6-[2''-3'-cyclohexyl-5'-tert-butyl-4'-hydroxyhydrocinnamoyloxy)ethylthio]norbornane.

1,2-di(3',5'-di-tert-butyl-4'-hydroxyhydrocinnamoyloxymethyl)-4-[2''-(3',5'-di-tert-butyl-4'-hydroxyhydrocinnamoyloxy)ethylthio]cyclohexane.

2,3-di(3',5'-di-tert-butyl-4'-hydroxyhydrocinnamoyloxymethyl)-5-[2''-(3',5'-di-tert-butyl-4'-hydroxyhydrocinnamoyloxy)ethylthio]bicyclo[2.2.2]octane.

The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, α,β-unsaturated acids, α,β-unsaturated esters, α,β-unsaturated ketones, α,β-unsaturated aldehydes and unsaturated hydrocarbons such as butadienes and styrene; poly-α-olefins such as high and low density polyethylene, crosslinked polyethylene polypropylene, poly(4-methyl-pentene-1) and the like, include copolymers of α-olefins; such as ethylene/propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene) azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethylene glycol, octaethyleneglycol, dibutyleneglycol, dipropyleneglycol and the like.

The compounds of this invention are particularly useful as thermal antioxidants, especially for the protection of polyolefins, for instance, polyethylene, polypropylene, poly(butene-1), poly(pentene-1), poly(3-methylbutene-1), poly(4-methylpentene-1), various ethylene/propylene and ethylene/propylene/diene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfurcontaining esters such as distearyl β-thiodipropionate (DSTDP), dilauryl β-thiodipropionate (DLTDP) in an amount of from 0.01 to 2% by weight of the organic material, and the like, pourpoint depressants, corrosion and rust inhibitors, dispersing agents, emulsifiers, antifoaming agents, fillers such as glass or other fibers, carbon black, accelerators and the other chemicals used in rubber compounding, plasticizers, color stabilizers, di- and tri-alkyl- and alkylphenylphosphites, heat stabilizers, ultraviolet light stabilizers, antiozonants, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

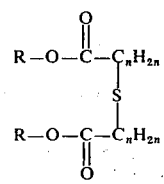

wherein R is an alkyl group having from 6 to 24 carbon atoms; and n is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.01 to 1%. Illustrative examples of light stabilizers are listed below.

UV-Absorbers and light protection agents 2-(2'-hydroxyphenyl)-benztriazoles, such as, for example, the 5'-methyl-, 3',5'-di-tert.-butyl-, 5'-tert.-butyl-, 5'(1,1,3,3-tetramethyl-butyl)-, 5-chloro-3',5'-di-tert.-butyl-, 5-chloro-3'-tert.-butyl-5'-methyl-, 3'-sec.-butyl-5'-tert.-butyl-, 3'-{α-methylbenzyl}-5'-methyl-, 3'-{α-methylbenzyl}-5'-methyl-5-chloro-, 4'-hydroxy-, 4'-methoxy-, 4'-octoxy-, 3',5'-di-tert.-amyl-, 3'-methyl-5'-carbomethoxyethyl- or 5-chloro-3',5'-di-tert.-amyl-derivative.

2,4-bis-(2'-hydroxyphenyl)-6-alkyl-s-triazines, such as, for example, the 6-ethyl-, 6-undecyl- or 6-heptadecyl-derivative.

2-hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

1,3-bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.

Esters of optionally substituted benzoic acids, such as, for example, phenyl salicylate, octylphenyl salicylate, di-benzoylresorcinol, bis-(4-tert.-butyl-benzoyl)-resorcinol, benzoyl-resorcinol, 3,5-di-tert.-butyl-4-hydroxybenzoic acid 2,4-di-tert.-butyl-phenyl ester, octadecyl ester or 2-methyl-4,6-di-tert.-butyl-phenyl ester.

Acrylates, such as, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

Nickel compounds, such as, for example, nickel complexes of 2,2'-thio-bis-4-(1,1,3,3-tetramethylbutyl)-phenol such as the 1:1 and 1:2 complex, optionally with other ligands such as n-butylamine, triethanolamine or N-cyclohexyl-diethanolamine; nickel complexes of bis-{2-hydroxy-4-(1,1,3,3-tetramethylbutyl)-phenyl}-sulphone, such as the 2:1 complex, optionally with other ligands such as ethyl-caproic acid; nickel dibutyldithiocarbamate, nickel salts of 4-hydroxy-3,5-di-tert.-butylbenzyl-phosphonic acid monoalkyl esters, such as the methyl, ethyl or butyl ester, the nickel complex of (2-hydroxy-4-methyl-phenyl)-undecyl-ketonoxime and nickel 3,5-di-tert.-butyl-4-hydroxy-benzoate.

Oxalic acid diamides, such as, for example, 4,4'-di-octyloxyoxanilide, 2,2'-dioctyloxy-5,5'-di-tert.-butyl-oxanilide, 2,2'-di-dodecyloxy-5,5'-di-tert.-butyl oxanilide, 2-ethoxy-5-tertiarybutyl-2'-ethyl-oxanilide, 2-ethoxy-2'-ethyl-oxanilide, N,N'-bis-(3-dimethylaminopropyl) oxalamide, mixtures of o- and p-methoxy and o- and p-ethoxy-di-substituted oxanilides and mixtures of 2-ethoxy-5-tert.-butyl 2'-ethyl-oxanilide with 2-ethoxy-2'-ethyl-5,4'-di-tert.-butyl-oxanilide.

Sterically hindered amines, such as, for example 4-benzoyloxy-2,2,6,6-tetramethylpiperidine, 4-stearoyloxy-2,2,6,6-tetramethylpiperidine, bis-(2,2,6,6-tetramethylpiperidyl) sebacate and 3-n-octyl-7,7,9,9-tetramethyl-1,3-triaza-spiro[4,5]decane-2,4-dione.

Especially useful compounds of this type are 2(2'-hydroxy-3',5'-di-tert-butylphenyl)-5-chlorobenzotriazole, 2-hydroxy-4-methoxy-5-sulfobenzophenone trihydrate, 2-hydroxy-4-n-octoxybenzophenone, [2,2'-thiobis(4-t-octylphenolate)]-n-butylamine nickel II, p-octylphenyl salicylate, 2,2'-dihydroxy-4,4'-dimethoxybenzophenone, and 2[2'-hydroxy-5'-methylphenyl]-benzotriazole.

The following examples further illustrate the present invention without introducing any limitations. The temperatures are in degrees centigrade.

EXAMPLE 1

2-(3',5'-di-tert-butyl-4'-hydroxyhydrocinnamoyloxymethyl)-5 or
6-[2''-(3',5'-di-tert-butyl-4'-hydroxyhydrocinnamoyloxy)ethylthio]norbornane a. 2-Methylol-5 or 6-(2'-hydroxyethylthio)norbornane In a nitrogen atmosphere, to a stirred solution of 12.4 grams (0.1 mole) of 2-hydroxymethyl-5-norbornene in 100 ml of dioxane was added in one portion 17.2 grams (0.22 mole) of 2-mercaptoethanol. The temperature rose from 25° to 50°. The mixture was then heated at 70° for 6.3 hours during which time a solution of 1.6 grams of α,α'-azobisisobutyronitrile in 20 ml of dioxane was added in portions. After standing overnight, the dioxane solvent and excess 2-mercaptoethanol were removed under reduced pressure. The residue was distilled to give the 2-methylol- 5 or 6-(2'-hydroxyethylthio)norbornane intermediate as a viscous oil with a boiling point of 140°–142°/0.05 mm in a yield of 15.0 grams (74%).

b. 2-(3', 5'-di-tert-butyl-4'-hydroxyhydrocinnamoyloxymethyl)-5 or 6-[2''-(3',5'-di-tert-butyl-4'-hydroxyhydrocinnamoyloxy)ethylthio]norbornane 10.1 grams (0.05 mole) of 2-methylol-5 or 6-(2'-hydroxyethylthio)norbornane was charged to a reactor equipped with a nitrogen inlet, stirrer and Dean-Stark trap topped with a dry-ice condenser. 100 mg of lithium hydride was added and the mixture heated at 50°C for 30 minutes under nitrogen. The mixture was cooled to 30°C and 29.2 grams (0.1 mole) of methyl 3,5-di-tert-butyl-4-hydroxyhydrocinnamate was added. The mixture was then heated to 110°C, and the temperature was gradually increased to 160°C over a 5.5 hour period. During this time 4.0 ml of methanol collected in the trap. 1.0 ml of acetic acid was added to the mixture when cooled, and the acidified mixture was dissolved in ether. The ether solution was washed with water, dried over anhydrous sodium sulfate and evaporated to dryness to yield 37.0 grams of a viscous oil. A 15.0 gram portion of this oil was chromatographed on 450 grams of silica gel using chloroform: ethyl acetate (19:1) solvent to give 6.4 grams of pure diester product as a viscous oil which was freed from solvent by heating at 95°C/0.05 mm for 17 hours. (Stabilizer No. 1)

Analysis for $C_{44}H_{66}O_6S$: Calculated: C, 73.09; H, 9.20. Found: C, 73.13; H, 8.95.

In like manner, by substituting an equivalent amount of methyl 3,5-di-tert-butyl-4-hydroxyphenylacetate for methyl 3,5-di-tert-butyl-4-hydroxyhydrocinnamate, the product 2-(3',5'-di-tert-butyl-4'-hydroxyphenylacetoxymethyl)-5 or 6-[2''-(3',5'-di-tert-butyl-4'-hydroxyphenylacetoxy)ethylthio]norbornane is obtained.

EXAMPLE 2

2-(3'-methyl-5'-tert-butyl-4'-hydroxyhydrocinnamoyloxymethyl)-5 or
6-[2''-(3'-methyl-5'-tert-butyl-4'-hydroxyhydrocinnamoyloxy)ethylthio]norbornane This compound was made in substantially the same manner as described in Example 1 by substituting methyl 3-methyl-5-tert-butyl-4-hydroxyhydrocinnamate for methyl 3,5-di-tert-butyl-4-hydroxyhydrocinnamate. The product was a viscous oil.

(Stabilizer No. 2)

Analysis for $C_{38}H_{54}O_6S$: Calculated: C, 71.43; H, 8.52; S, 5.02. Found: C, 71.93; H, 8.51; S, 4.79.

If in Example 1, 2-mercaptoethanol is replaced by an equivalent amount of 6-mercaptohexanol, and methyl 3,5-di-tert-butyl-4-hydroxyhydrocinnamate is replaced by methyl 3-methyl-5-tert-butyl-4-hydroxyhydrocinnamate the product 2-(3'-methyl-5'-tert-butyl-4'-hydroxyhydrocinnamoyloxymethyl)-5 or 6-[6'''-(3'-methyl-5'-tert-butyl-4'-hydroxyhydrocinnamoyloxy)hexylthio]-norbornane is obtained.

If in Example 1, methyl 3,5-di-tert-butyl-4-hydroxyhydrocinnamate is replaced by an equivalent amount of methyl 2,3-dimethyl-5-tert-butyl-4-hydroxyhydrocinnamate, the product 2-(2',3'-dimethyl-5'-tert-butyl-4'-hydroxyhydrocinnamoyloxymethyl)-5 or 6-[2''-(2',3'-dimethyl-5'-tert-butyl-4'hydroxycinnamoyloxy)ethylthio]norbornane is obtained.

EXAMPLE 3

2,2-di(3',5'-di-tert-butyl-4'-hydroxyhydrocinnamoyloxymethyl)-5 or
6-[2''-(3',5'-di-tert-butyl-4'-hydroxyhydrocinnamoyloxy)ethylthio]norbornane.

This compound was made in substantially the same manner as described in Example 1 except that 2-hydroxymethyl-5-norbornene is replaced by an equivalent amount of 2,2-dimethylol-5-norbornene. The intermediate sulfide obtained was used without further purification for the subsequent transesterification step with methyl 3,5-di-tert-butyl-4-hydroxyhydrocinnamate to yield the desired product as a glassy material.

(Stabilizer No. 3)

Analysis for $C_{62}H_{92}O_9S$: Calculated: C, 73.48; H, 9.15; S, 3.16. Found: C, 73.31; H, 9.33; S, 3.36.

If in this example, methyl 3,5-di-tert-butyl-4-hydroxyhydrocinnamate is replaced by an equivalent amount of methyl 3,5-di-tert-butyl-4-hydroxyphenylacetate, the product 2,2-di(3',5'-di-tert-butyl-4'-hydroxyphenylac toxymethyl)-5 or 6-[2''-(3',5'-di-tert-butyl-4'-hydroxyphenylacetoxy)ethylthio]norbornane is obtained.

If in this example, methyl 3,5-di-tert-butyl-4-hydroxyhydrocinnamate is replaced by an equivalent amount of methyl 2,6-dimethyl-4-tert-butyl-3-hydroxyphenylacetate, the product 2,2-di(2',6'-dimethyl-4'-tert-butyl-3'-hydroxyphenylacetoxymethyl)-5 or 6-[2''-(2',6'-dimethyl-4'-tert-butyl-3'-hydroxyphenylacetoxyethylthio]norbornane is obtained.

EXAMPLE 4

2,2-di(3'-methyl-5'-tert-butyl-4'-hydroxyhydrocinnamoyloxymethyl)-5 or
6-[2''-(3'-methyl-5'-tert-butyl-4'-hydroxyhydrocinnamoyloxy)ethylthio]norbornane If in Example 3, methyl 3,5-di-tert-butyl-4-hydroxyhydrocinnamate was replaced by an equivalent amount of methyl 3-methyl-5-tert-butyl-4-hydroxyhydrocinnamate, the desired product was obtained as a glassy material.

(Stabilizer No. 4)

Analysis for $C_{53}H_{74}O_9S$: Calculated: C, 71.75; H, 8.41. Found: c, 71.49; H, 8.29.

EXAMPLE 5

2,3-di(3',5'-di-tert-butyl-4'-hydroxyhydrocinnamoyloxymethyl)-5-[2''-(3',5'-di-tert-butyl-4'-hydroxyhydrocinnamoyloxy)ethylthio]norbornane If in Example 3, 2,2-dimethylol-5-norbornene was replaced by an equivalent amount of 2,3-dimethylol-5-norbornene, the desired product was obtained as a glassy material.

(Stabilizer No. 5)

Analysis for $C_{62}H_{92}O_9S$: Calculated: C, 73.48; H, 9.15. Found: C, 73.18; H, 9.23.

If in Example 3, 2,2-dimethylol-5-norbornene is replaced by an equivalent amount of cyclohex-4-ene-1,2-dimethanol, the product 1,2-di(3',5'-di-tert-butyl-4'-hydroxyhydrocinnamoyloxymethyl)-4-[2''-(3',5'-di-tert-butyl-4'-hydroxyhydrocinnamoyloxy)ethylthio]cyclohexane is obtained.

If in Example 3, 2,2-dimethylol-5-norbornene is replaced by an equivalent amount of bicyclo[2.2.2]oct-5-ene-2,3-dimethanol, the product 2,3-di(3',5'-di-tert-butyl-4'-hydroxyhydrocinnamoyloxymethyl)-5-[2''-(3',5'-di-tert-butyl-4'-hydroxyhydrocinnamoyloxy)ethylthio]-bicyclo[2.2.2]octane is obtained.

EXAMPLE 6

2,3-di(3'-methyl-5'-tert-butyl-4'-hydroxyhydrocinnamoyloxymethyl)-5-[2''-(3'-methyl-5'-tert-butyl-4'-hydroxyhydrocinnamoyloxy)ethylthio]-norbornane If in Example 3, 2,2-dimethylol-5-norbornene was replaced by an equivalent amount of 2,3-dimethylol-5-norbornene, and the methyl 3,5-di-tert-butyl-4-hydroxyhydrocinnamate was replaced by methyl 3-methyl-5-tert-butyl-4-hydroxyhydrocinnamate, the desired product was obtained as a glassy material.

(Stabilizer No. 6)

Analysis for $C_{53}H_{74}O_9S$: Calculated: C, 71.75; H, 8.41; S, 3.61. Found: C, 71.81; H, 8.54; S, 3.65.

EXAMPLE 7

A batch of unstabilized polypropylene powder (Hercules Profax 6501) was thoroughly blended with 0.2% by weight of various compounds of this invention. The blended materials are then milled on a two-roll mill at 182°C for 5 minutes after which time the stabilized polypropylene was sheeted from the mill and allowed to cool.

The milled polypropylene sheets were than cut into pieces and pressed for 5 minutes on a hydraulic press at 218°C and 19.25 Kg/cm$^2$ pressure. The resulting plaques of 0.635 mm thickness were tested for resistance to accelerated aging in a forced draft oven at 150°C. When the plaques showed the first signs of decomposition (eg. cracking or brown edges), they were considered to have failed. The results are set out in Table 1.

Table 1

| Stabilizer No. | Oven Aging at 150°C Hours to Failure |
|---|---|
| 1 | 1075 |
| 2 | 1140 |
| 3 | 1070 |
| 4 | 620 |
| 5 | 830 |
| 6 | 540 |
| Unstabilized Polypropylene | 3 |

EXAMPLE 8

Test specimens were prepared exactly as described in Example 7 except that the stabilized polypropylene contained 0.2% by weight of the various compounds of this invention and 0.5% by weight of 2(2'-hydroxy-3',-5'-di-tert-butylphenyl)-5-chlorobenzotriazole as a co-stabilizer. Results of accelerated aging tests in a forced draft oven at 150°C are shown in Table 2.

Table 2

| Stabilizer No. (Plus Co-Stabilizer) | Oven Aging at 150°C Hours to Failure |
|---|---|
| 1 | 1105 |
| 2 | 875 |
| 3 | 900 |
| 4 | 605 |
| 5 | 765 |
| 6 | 490 |
| Unstabilized Polypropylene | 3 |

EXAMPLE 9

Test specimens were prepared exactly as described in Example 7 except that the stabilized polypropylene contained 0.1% by weight of various compounds of this invention and 0.3% by weight of distearyl thiodipropionate (DSTDP) as a co-stabilizer. Results of accelerated aging tests in a forced draft oven at 150°C are shown on Table 3.

Table 3

| Stabilizer No. (Plus Co-Stabilizer) | Oven Aging at 150°C Hours to Failure |
|---|---|
| 1 | 1660 |
| 2 | 2100 |
| 3 | 1740 |
| 4 | 1785 |
| 5 | 1270 |
| 6 | 1225 |
| Unstabilized Polypropylene | 3 |
| With DSTDP Only | 100 |

EXAMPLE 10

Test specimens were prepared exactly as those described in Example 8 except that the milled polypropylene sheets were cut into pieces and pressed for 3 minutes on a hydraulic press at 218°C and 19.25 Kg/cm² pressure. The resulting sheet of 0.127 mm thickness was tested in a fluorescent sunlight black light environment with the development of carbonyl absorption in the infrared spectrum at the 585 millimicron wavelength being the measure of stabilization protection afforded by the stabilizers present in the polypropylene. Failure was taken as the hours required to cause the carbonyl absorption to reach a value of 0.5. Such a value correlates with the reduction of physical properties of the polypropylene pellicle to unacceptable levels. The results are set out in Table 4.

Table 4

| Stabilizer No. (Plus Co-Stabilizer) | Fluorescent Sunlight Black Light Test Hours to Failure (0.5 Carbonyl Absorption) |
|---|---|
| 1 | 895 |
| 2 | 645 |
| 3 | 775 |
| 4 | 525 |
| 5 | 560 |
| 6 | 405 |
| Unstabilized Polypropylene | 225 |

EXAMPLE 11

Pellets (500 g) of unstabilized nylon-6,6 (Zytel 101, DuPont) are placed in a Kitchen Aid Mixer. With mixing a solution of 0.5% (based on the weight of nylon) of 2-(3',5'-di-tert-butyl-4'-hydroxyhydrocinnamoyloxymethyl)-5 or 6-[2''-(3',5'-di-tert-butyl-4'-hydroxyhydrocinnamoyloxy)ethylthio]norbornane in 20 ml of methylene chloride is added slowly. Sodium hypophosphite (0.5 gm 0.1%) is dissolved in 20 ml of water and added slowly with mixing to the nylon pellets after the antioxidant solution has been added and most of the methylene chloride has evaporated. The stabilized pellets are dried at 80°C at <1 mm Hg. for 4 hours.

The polyamide formulation is extruded at 315.6°C through at 0.635 cm die into a rod which is water cooled and chopped into pellets. A 1.905 cm Brabender extruder, equipped with a nylon screw, is used. The pellets are dried at 80°C at <1 mm for 4 hours.

The dried pellets are compression molded into 0.127 mm thick film by pressing at 290°C for 4 minutes at 57.75 Kg/cm². The films are oven aged at 150°C in a forced draft oven and samples are removed periodically. The specific viscosity of the samples are determined using a 1% formic acid solution at 25°C. The sample stabilized with the above noted stabilizer required longer aging time to reduce its viscosity by one-half than the unstabilized sample.

EXAMPLE 12

Unstabilized high impact polystyrene resin is dry blended with 0.01% by weight of the resin of 2-(3'-methyl-5'-tert-butyl-4'-hydroxyhydrocinnamoyloxymethyl)-5 or 6-[2''-(3'-methyl-5'-tert-butyl-4'-hydroxyhydrocinnamoyloxy)ethylthio]norbornane.

The resin is then extrusion compounded on a 2.54 cm 24/1=L/D extruder at melt temperature 260°C and pressed for 7 minutes at a temperature of 163°C and a pressure of 140 Kg/cm² into a sheet of uniform thickness of 0.752 mm. The sheets are then cut into plaques of 5.08 cm × 5.08 cm × 0.752 mm. The plaques are then oven aged at 80°C and color measurements made periodically using a Hunter Color Difference meter Model D25. The polystyrene samples stabilized with the above stabilizer develops the undesirable yellow discoloration substantially later than the time that such discoloration occurred in the unstabilized samples.

EXAMPLE 13

Unstabilized linear polyethylene (HiFax 4401) is solvent blended in methylene chloride with 0.2% by weight of the substrate of 2,2-di(3',5'-di-tert-butyl-4'-hydroxyhydrocinnamoyloxymethyl)-5 or 6-[2''-(3',5'-di-tert-butyl-4'-hydroxyhydrocinnamoyloxy)ethylthio]norbornane and then vacuum dried. The resin is then extruded at 287.8°C using a 1.905 cm extruder having a 24:1 L/D ratio. The melt flow rate of a sample of the resin is determined after each extrusion according to ASTM test D-1238. Polyethylene stabilized with above compound is found to undergo less change in the melt flow rate than the unstabilized polyethylene.

What is claimed is:

1. A compound having the formula I

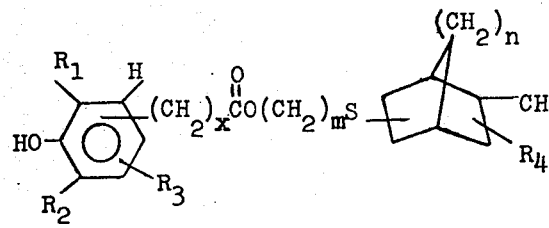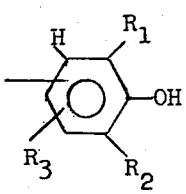

wherein $R_1$ and $R_2$ are independently the same or different alkyl groups of from 1 to 8 carbon atoms, cycloalkyl of from 5 to 6 carbon atoms or one of $R_1$ and $R_2$ is hydrogen, $R_3$ is hydrogen or lower alkyl of from 1 to 6 carbon atoms, providing that $R_3$ may be in either the meta or para position of the aromatic ring relevant to the hydroxyl group and that the side chain groups

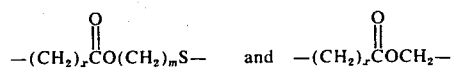

are located on the carbon adjacent to that of the $R_3$ group, $R_4$ is hydrogen or a group

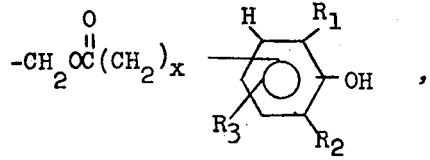

$m$ has a value of 2 to 6,
$n$ has a value of 0 to 2, and
$x$ has a value of 1 to 2.

2. A compound of claim 1 wherein
$R_1$ and $R_2$ are methyl, isopropyl or tert-butyl,
$R_3$ is hydrogen or methyl,
$m$ has a value of 2 to 6, and
$n$ has a value of 1.

3. A compound of claim 1 wherein $R_1$ is tert-butyl, $R_2$ is tert-butyl or methyl, $R_3$ is hydrogen or methyl, $m$ has a value of 2, $n$ has a value of 1, and $x$ has a value of 2.

4. The compound according to claim 1 which is 2-(3',5'-di-tert-butyl-4'-hydroxyhydrocinnamoyloxymethyl)-5 or 6-[2''-(3',5'-di-tert-butyl-4'-hydroxyhydrocinnamoyloxy)ethylthio]norbornane.

5. The compound according to claim 1 which is 2-(3'-methyl-5'-tert-butyl-4'-hydroxyhydrocinnamoyloxymethyl)-5 or 6-[2''-(3'-methyl-5'-tert-butyl-4'-hydroxyhydrocinnamoyloxy)ethylthio]norbornane.

6. The compound according to claim 1 which is 2,2-di-(3',5'-di-tert-butyl-4'-hydroxyhydrocinnamoyloxymethyl)-5 or 6-[2''-(3',5'-di-tert-butyl-4'-hydroxyhydrocinnamoyloxy)ethylthio]norbornane.

7. The compound according to claim 1 which is 2,2-di(3'-methyl-5'-tert-butyl-4'-hydroxyhydrocinnamoyloxymethyl)-5 or 6-[2''-(3'-methyl-5'-tert-butyl-4'-hydroxyhydrocinnamoyloxy)ethylthio]norbornane.

8. A compound according to claim 1 which is 2,3-di(-3',5'-di-tert-butyl-4'-hydroxyhydrocinnamoyloxymethyl)-5-[2''-(3',5'-di-tert-butyl-4'-hydroxyhydrocinnamoyloxy)ethylthio]norbornane.

9. A compound according to claim 1 which is 2,3-di(-3'-methyl-5'-tert-butyl-4'-hydroxyhydrocinnamoyloxymethyl)-5-[2''-(3'-methyl-5'-tert-butyl-4'-hydroxyhydrocinnamoyloxy)ethylthio]norbornane.

10. A compound according to claim 1 which is 2-(3',5'-di-tert-butyl-4'-hydroxyphenylacetoxymethyl)-5 or 6-[2''-(3',5'-(3',5'-di-tert-butyl-4'-hydroxyphenylacetoxy)ethylthio]norbornane.

11. A compound according to claim 1 which is 2-(2,3'-dimethyl-5'-tert-butyl-4' hydroxyhydrocinnamoyloxy-methyl)-5 or 6-[2''-(2'',3'-dimethyl-5'-tert-butyl-4'-hydroxyhydrocinnamoyloxy)ethylthio]-norbornane.

* * * * *